(12) United States Patent
Hsiao

(10) Patent No.: US 10,603,399 B2
(45) Date of Patent: Mar. 31, 2020

(54) FRAGRANCE DELIVERY APPARATUS

(71) Applicant: DONGGUAN YIH TEH ELECTRIC PRODUCTS CO., LTD., Dongguan, Guangdong (CN)

(72) Inventor: Ming Jen Hsiao, Miaoli County (TW)

(73) Assignee: DONGGUAN YIH TEH ELECTRIC PRODUCTS CO., LTD., Dongguan (CN)

(*) Notice: Subject to any disclaimer, the term of this patent is extended or adjusted under 35 U.S.C. 154(b) by 139 days.

(21) Appl. No.: 15/893,962

(22) Filed: Feb. 12, 2018

(65) Prior Publication Data
US 2019/0247531 A1 Aug. 15, 2019

(51) Int. Cl.
*A61L 9/12* (2006.01)
*B01F 3/04* (2006.01)
*F24F 1/02* (2019.01)

(52) U.S. Cl.
CPC ............ *A61L 9/122* (2013.01); *B01F 3/04* (2013.01); *F24F 1/02* (2013.01); *A61L 2209/12* (2013.01); *A61L 2209/13* (2013.01)

(58) Field of Classification Search
CPC . B01F 3/04; B01D 46/24; B01D 35/30; F24F 1/02
USPC .................................................. 96/417, 222
See application file for complete search history.

(56) References Cited

U.S. PATENT DOCUMENTS

| D620,574 S | 7/2010 | Jorgensen |
| 7,963,460 B2 | 6/2011 | Jorgensen |
| 8,201,957 B2 | 6/2012 | Hsiao |

FOREIGN PATENT DOCUMENTS

| CN | 204534873 U | * | 8/2015 | ............... F24F 1/02 |
| CN | 205119264 U | * | 3/2016 | ............... F24F 1/02 |

* cited by examiner

*Primary Examiner* — Robert A Hopkins
(74) *Attorney, Agent, or Firm* — Chun-Ming Shih; Lanway IPR Services

(57) ABSTRACT

A fragrance delivery apparatus contains: a body, a fan, a power base, and a case. The body includes an accommodation chamber defined therein, a receiving groove formed above the accommodation chamber, an air vent arranged on a first side of the body and communicating between the accommodation chamber and the receiving groove, and multiple elongated orifices formed on a second side of the body opposite to the first side of the body and communicating with the accommodation chamber. The fan is accommodated in the accommodation chamber and draws external gas from the multiple elongated orifices. The power base is connected with the body and shields the accommodation chamber, and the power base is configured to supply power and is electrically connected with the fan. The case is removably connected outside the body and includes a spray nozzle which is in communication with the receiving groove.

20 Claims, 4 Drawing Sheets

FRAGRANCE DELIVERY APPARATUS

FIELD OF THE INVENTION

The present invention relates to a fragrance delivery apparatus.

DESCRIPTION OF THE PRIOR ART

A conventional fragrance diffuser disperses scents slowly in a limited range as disclosed in U.S. Pat. No. D620,574. A conventional detachable aromatic nebulizing diffuser is disclosed in U.S. Pat. No. 7,963,460 and contains a fan configured to deliver scents toward an external space, but it consumes power of two electric devices. A lamp-based scent releasing system is disclosed in U.S. Pat. No. 8,201,957 and contains a heating element configured to heat aromatic substance, for example, an electric resistance heats the aromatic substance so as to diffuse power, thus causing power consumption.

The present invention has arisen to mitigate and/or obviate the afore-described disadvantages.

SUMMARY OF THE INVENTION

The primary aspect of the present invention is to provide a fragrance delivery apparatus which is safe and save power.

To obtain the above aspect, a fragrance delivery apparatus provided by the present invention contains: a body, a fan, a power base, and a case.

The body includes an accommodation chamber defined in the body, a receiving groove formed above the accommodation chamber, an air vent arranged on a first side of the body and communicating between the accommodation chamber and the receiving groove, and multiple elongated orifices formed on a second side of the body opposite to the first side of the body and communicating with the accommodation chamber of the body.

The fan is accommodated in the accommodation chamber and draws external gas from the multiple elongated orifices.

The power base is connected with a bottom of the body and shields the accommodation chamber, and the power base is configured to supply power and is electrically connected with the fan.

The case being removably is connected outside the body and including a spray nozzle defined on a side of the case, wherein the spray nozzle is in communication with the receiving groove.

The power base supplies the power to the fan so that the fan runs and delivers gas into the accommodation chamber from the multiple elongated orifices of the body and flows through the fan, the solid fragrance member of the receiving groove and the air vent, wherein the solid fragrance member absorbs the aromatic substance (such as aromatic volatile liquid, essential oil, aromatic essence, flower essence, perfume, and air freshener) and the aromatic substance is guided by the gas to diffuse toward the external space via the spray nozzle. Accordingly, the fragrance delivery apparatus is simplified (for example, a heating element or a liquid oscillator is not required) so as to diffuse the aromatic substance by way of the fan, thus dispensing scents easily and safely.

The solid fragrance member is housed in the receiving groove of the fragrance delivery apparatus and is configured to absorb the aromatic substance.

The solid fragrance member has the bored carrier made of solid material, such as plastic, polyethylene (PE), ceramics, plaster, stone, foam, or wood. The solid fragrance member aborts the aromatic substance, such as the aromatic volatile liquid, the essential oil, the aromatic essence, the flower essence, the perfume, and the air freshener. Preferably, any one of the essential oil, the aromatic essence, the flower essence, the perfume, and the air freshener mixes with volatile substance so as to volatile fragrance molecules, thus diffusing the scents.

The bored carrier of the solid fragrance member has multiple through orifices passing through two ends of the bored carrier, and the bored carrier is configured to absorb the aromatic substance, such that the gas flows through the multiple through orifices so as to absorb the aromatic substance on the bored carrier. Preferably, an area of the bored carrier contacting with the gas is increased by way of the bored carrier so as to facilitate volatilization of the aromatic substance.

DETAILED DESCRIPTION OF THE PREFERRED EMBODIMENTS

Figure 1:
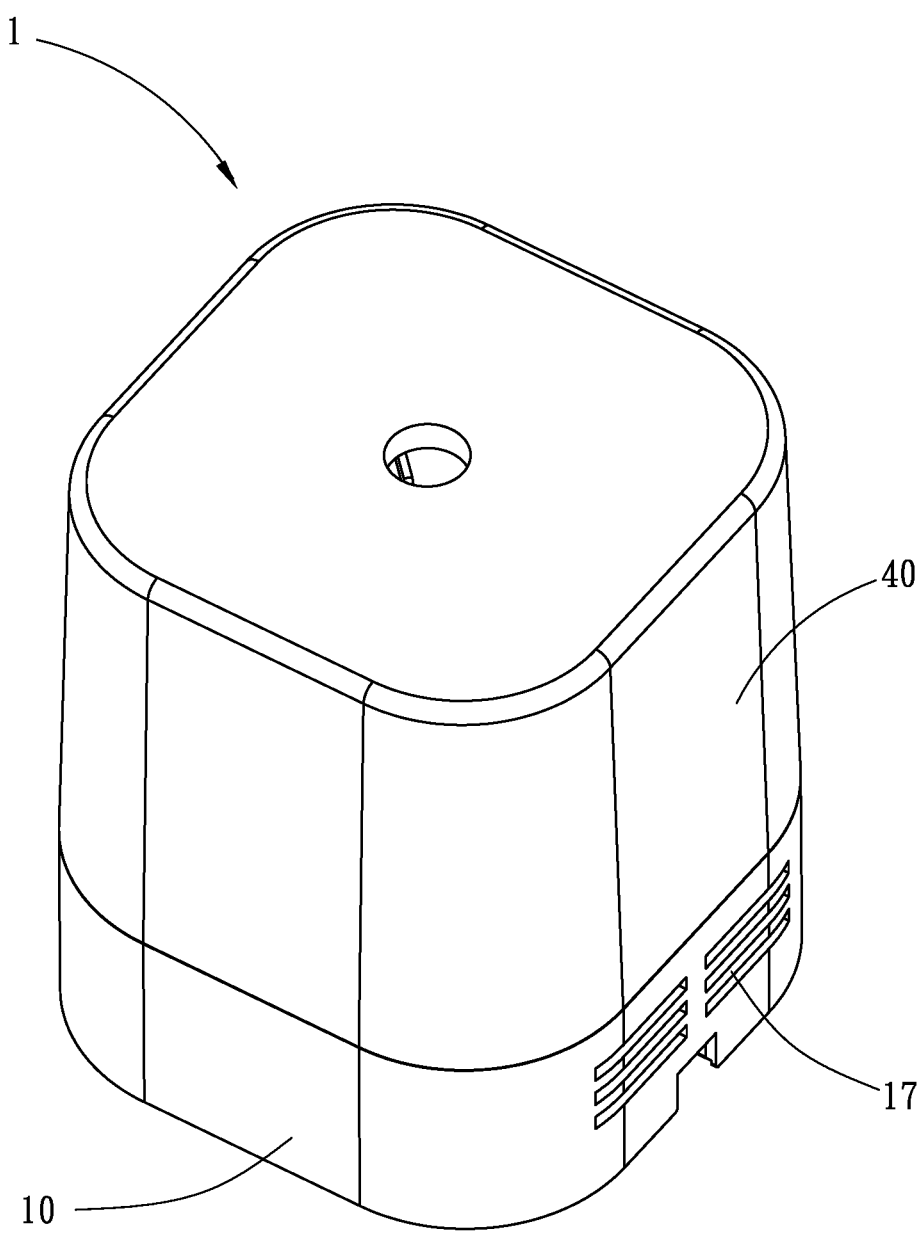
FIG. 1 is a perspective view showing the assembly of a fragrance delivery apparatus according to a preferred embodiment of the present invention.

With reference to FIGS. 1-4, a fragrance delivery apparatus 1 according to a preferred embodiment of the present invention comprises: a body 10, a fan 20, a power base 30, and a case 40.

The body 10 includes an accommodation chamber 11 defined therein, a receiving groove 13 formed above the accommodation chamber 11, an air vent 15 arranged on a first side of the body 10 and communicating between the accommodation chamber 11 and the receiving groove 13, and multiple elongated orifices 17 formed on a second side of the body 10 opposite to the first side of the body 10 and communicating with the accommodation chamber 11 of the body 10.

The fan 20 is accommodated in the accommodation chamber 11 and draws external gas from the multiple elongated orifices 17.

The power base 30 is connected with a bottom of the body 10 and shields the accommodation chamber 11. The power base 30 is configured to supply power and is electrically connected with the fan 20.

The case 40 is removably connected outside the body 10 and includes a spray nozzle 401 defined on a side of the case 40, wherein the spray nozzle 401 is in communication with the receiving groove 13 and an external space.

Thereby, a solid fragrance member 12 is housed in the receiving groove 13 of the body 10 of the fragrance delivery apparatus 1 and is configured to absorb aromatic substance.

The power base 30 supplies the power to the fan 20 so that the fan 20 runs and delivers gas into the accommodation chamber 11 from the multiple elongated orifices 17 of the body 10 and flows through the fan 20, the solid fragrance member 12 of the receiving groove 13 and the air vent 15, wherein the solid fragrance member 12 absorbs the aromatic substance (such as aromatic volatile liquid, essential oil, aromatic essence, flower essence, perfume, and air freshener) and the aromatic substance is guided by the gas to diffuse toward the external space via the spray nozzle 401. Accordingly, the fragrance delivery apparatus 1 is simplified (for example, a heating element or a liquid oscillator is not required) so as to diffuse the aromatic substance by way of the fan, thus dispensing scents easily and safely.

Figure 2:
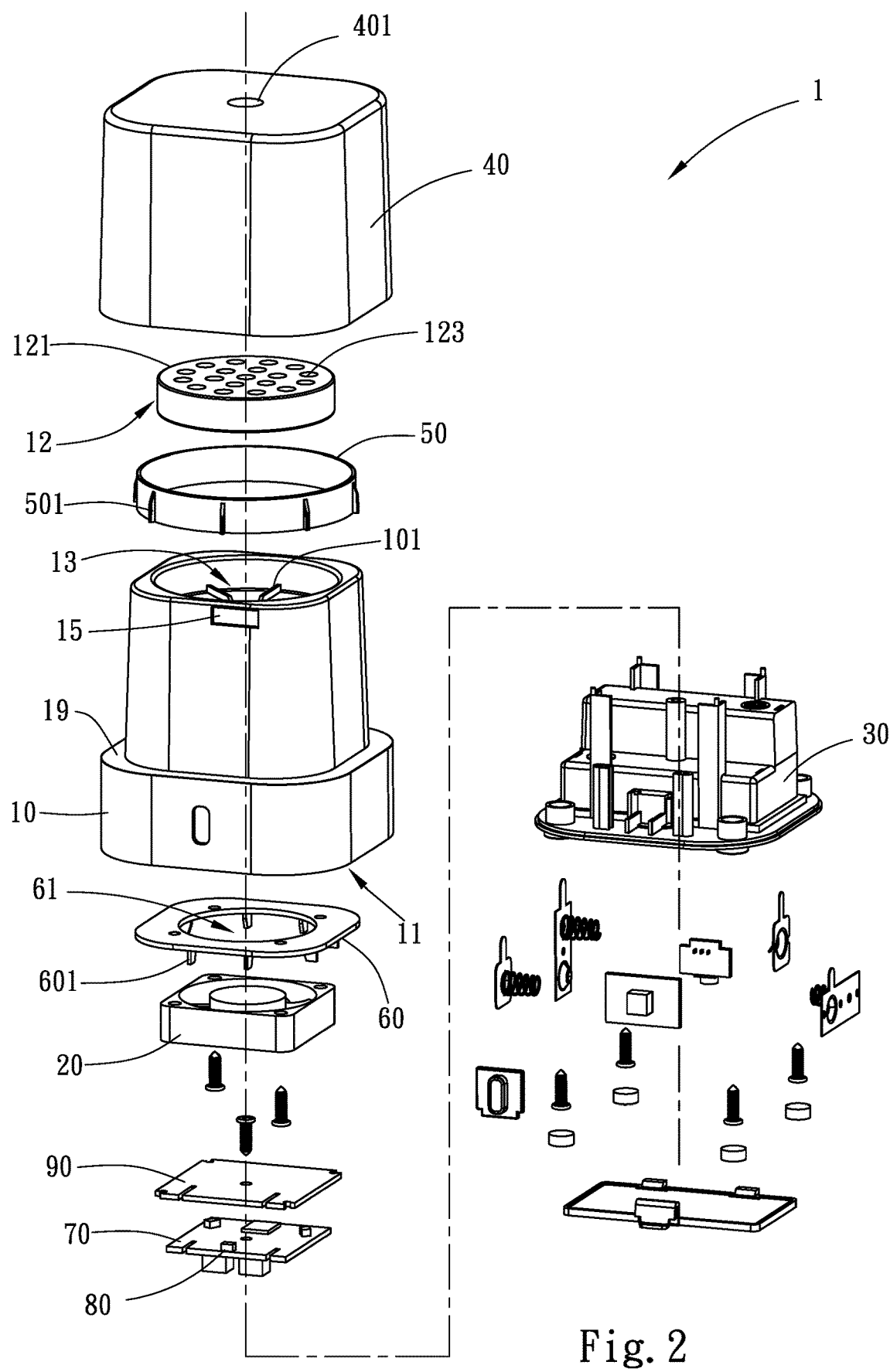
FIG. 2 is a perspective view showing the exploded components of the fragrance delivery apparatus according to the preferred embodiment of the present invention.
Figure 4:
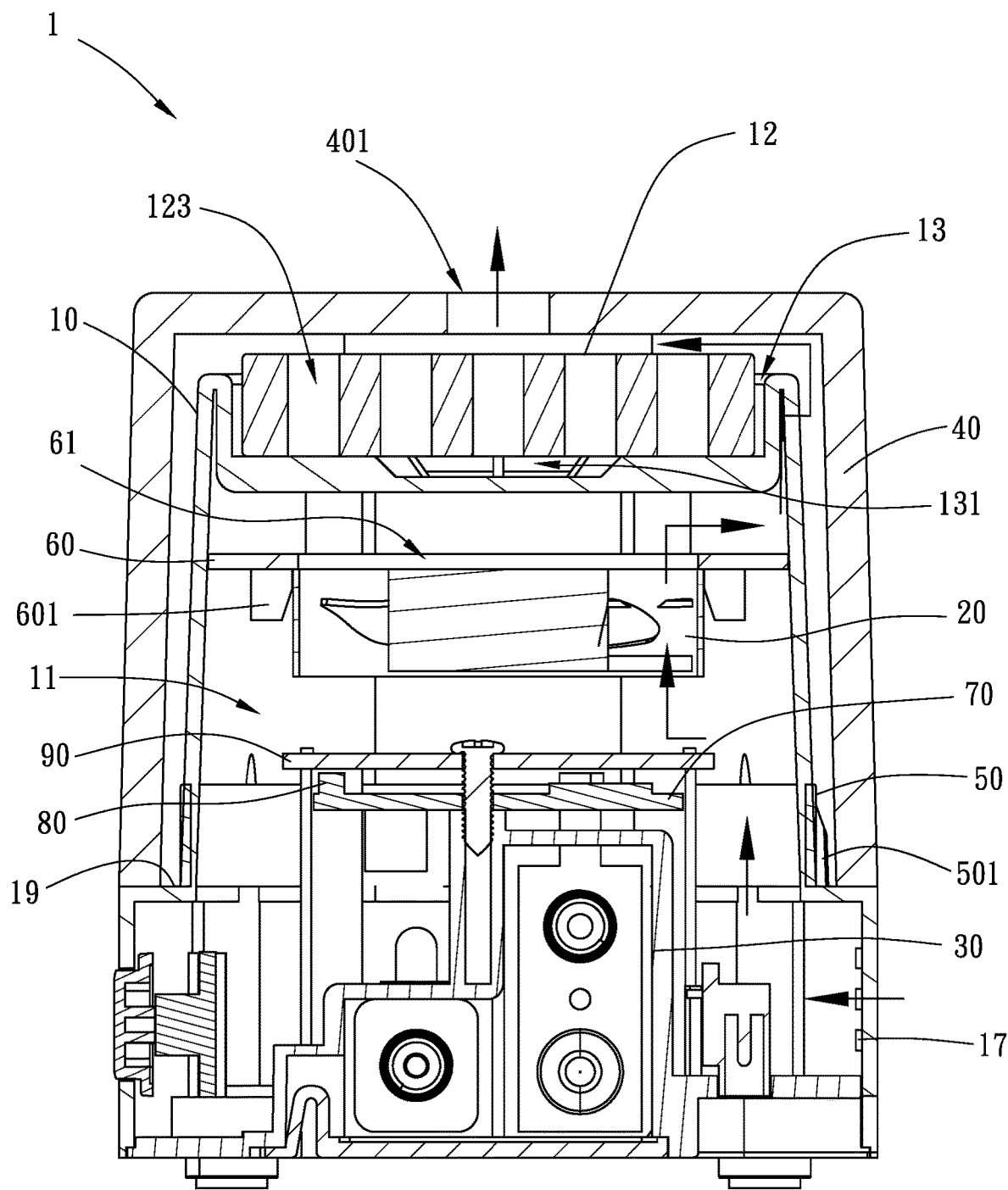
FIG. 4 is a cross sectional view taken along the line X-X of FIG. 3.

Referring further to FIGS. 2 and 4, the solid fragrance member 12 is housed in the receiving groove 13 of the fragrance delivery apparatus 1 and is configured to absorb the aromatic substance.

The solid fragrance member 12 has a bored carrier 121 made of solid material, such as plastic, polyethylene (PE), ceramics, plaster, stone, foam, or wood. The solid fragrance member 12 aborts the aromatic substance, such as the aromatic volatile liquid, the essential oil, the aromatic essence, the flower essence, the perfume, and the air freshener. Preferably, any one of the essential oil, the aromatic essence, the flower essence, the perfume, and the air freshener mixes with volatile substance so as to volatile fragrance molecules, thus diffusing the scents.

As shown in FIGS. 2 and 4, the bored carrier 121 of the solid fragrance member 12 has multiple through orifices 123 passing through two ends of the bored carrier 121, and the bored carrier 121 is configured to absorb the aromatic substance, such that the gas flows through the multiple through orifices 123 so as to absorb the aromatic substance on the bored carrier 121. Preferably, an area of the bored carrier 121 contacting with the gas is increased by way of the bored carrier 121 so as to facilitate volatilization of the aromatic substance. In this embodiment, any one of the essential oil, the aromatic essence, and the flower essence mixes with the volatile substance so as to volatile the aromatic substance. Preferably, the case 40 is removed so as to drop the aromatic substance onto the bored carrier 121 after the aromatic substance completely volatiles or exhausts, thus using the solid fragrance member 12 repeatedly.

As illustrated in FIGS. 2 and 4, the bored carrier 121 is made of PE so as to absorb the aromatic substance, and the gas flows through the multiple through orifices 123 so as to facilitate volatilization of the aromatic substance.

Figure 3:
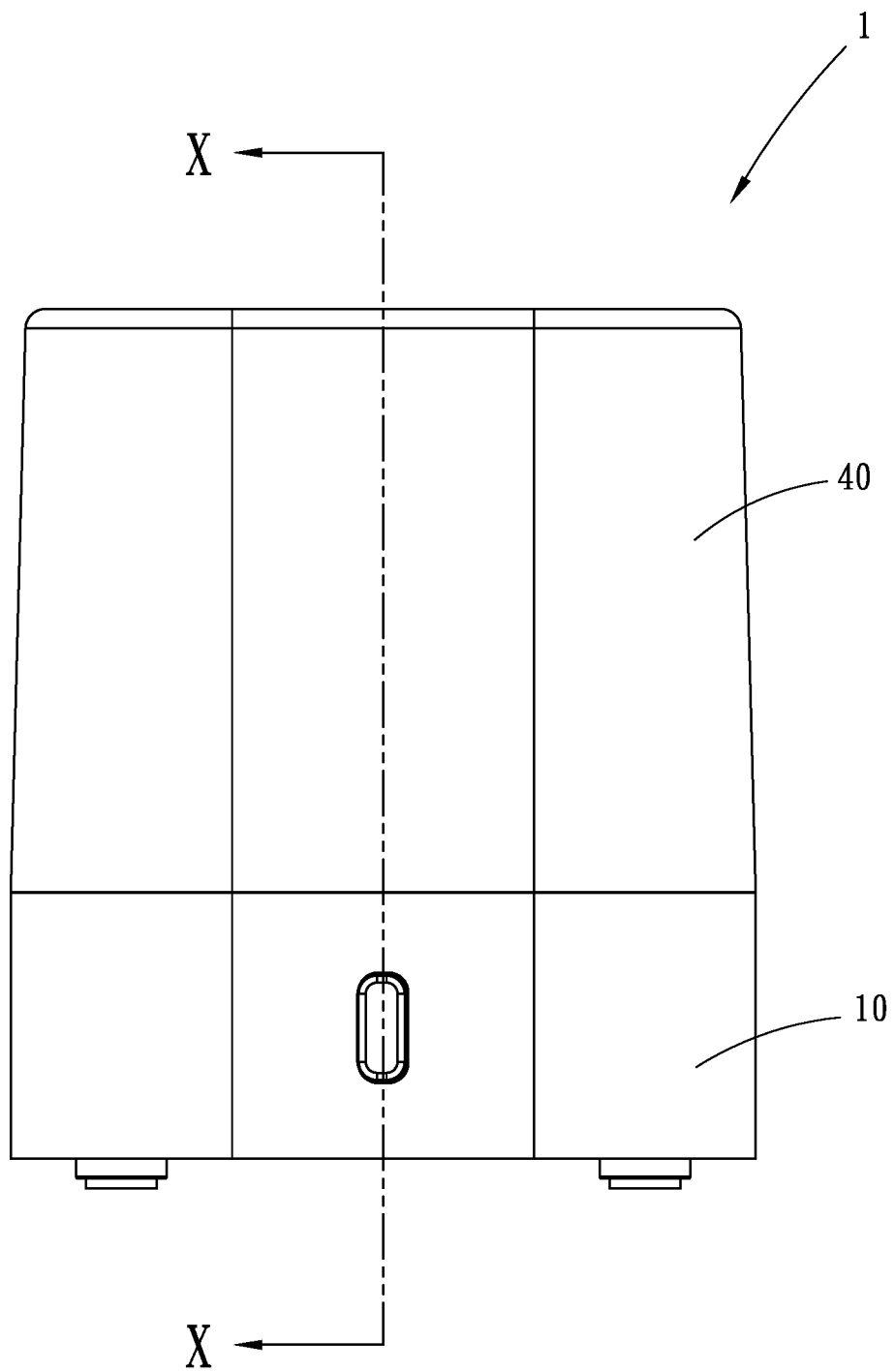
FIG. 3 is a side plan view showing the assembly of the fragrance delivery apparatus according to the preferred embodiment of the present invention.

With reference to FIGS. 3 and 4, the body 10 further includes a stepped portion 19 formed on an outer wall thereof, and the case 40 is hollow and covers on the outer wall of the body 10, wherein an inner wall of the case 40 is detachably connected on the body 10, and the stepped portion 19 matingly couples with a support loop 50 inside a bottom of the case 40.

Referring to FIGS. 2-4, the fragrance delivery apparatus 1 further comprises the support loop 50 including multiple abutting ribs 501 arranged around an outer wall of the support loop 50, the support loop 50 is fitted on the outer wall of the body 10 and the case 40 covers on the outer wall of the body 10, wherein an inner wall of the body 10 is detachably connected with the multiple abutting ribs 501 of the support loop 50, and the multiple abutting ribs 501 are flexible, such that when the case 40 covers on the outer wall of the body 10, the inner wall of the body 10 forces the multiple abutting ribs 501 to deform and to engage with the inner wall of the case 40, and the case 40 removably engages with the support loop 50, thus removing/covering the case 40 from/on the body 10.

With reference to FIGS. 2-4, the receiving groove 13 has multiple flaps 101 separately arranged on a bottom thereof, and the solid fragrance member 12 is placed on the multiple flaps 101, wherein a bottom of the solid fragrance member 12 separates a distance from the receiving groove 13 so that the gas flows through the bottom of the solid fragrance member 12, thus dispersing the aromatic substance effectively.

Referring to FIGS. 2-4, the receiving groove 13 has a recessed guiding portion 131 formed on the bottom thereof below the multiple flaps 101, when overly dropping the aromatic substance of the solid fragrance member 12 onto the bored carrier 121, the aromatic substance accumulates in the recessed guiding portion 131 so that the fan 20 blows the aromatic substance out of the spray nozzle 401.

The support loop 50 is made of flexible material, and the flexible material is any one of silicone, rubber, and plastic.

As shown in FIGS. 2 and 3, the fragrance delivery apparatus 1 further comprises a stop member 60 including an opening defined therein and mating with the fan 20, and the stop member 60 including multiple affix extensions 601 extending outwardly from a bottom of the stop member 60 so as to retain with the fan 20, wherein the stop member 60 is connected on the fan 20 and the opening 61 corresponds to the fan 20, such that a peripheral portion of the stop member 60 around the opening 61 couples with the inner wall of the body 10 so as to shield a gap between the opening 15 and the accommodation chamber 11, hence when the fan 20 blows the gas to the opening 15 and the receiving groove 13, a part of the gas is stopped by the opening 15 and the stop member 60, thus dispersing the aromatic substance by using the fan 20.

As shown in FIGS. 2 and 3, the fragrance delivery apparatus 1 further comprises a circuit board 70, a light emitting element 80, a light guide sheet 90, and a power switch 100.

The circuit board 70 is electrically connected with the fan 20, the power base 30, the light emitting element 80, and the power switch 100. The circuit board 70 is mounted on the power base 30 in the body 10, and the light guide sheet 90 is fixed on the circuit board 70 and covers the light emitting element 80. Each of the body 10 and the case 40 is made of transparent material or translucent material. After turning on the power switch 100, the power is supplied to the circuit board 70 from the power base 30 so as to power on the light emitting element 80, thus illuminating lights of various colors. The light guide sheet 90 is made of transparent material or translucent material, and the transparent material or translucent material is plastic or glass, such that the lights from the light emitting element 80 evenly spread on the light guide sheet 90 and diffuse through the body 10 and the case 40.

Since an atomizer (not shown) of the fragrance delivery apparatus 1 is in a small size and mates with the fan of a small size, the scents are atomized and sprayed effectively.

While the preferred embodiments of the invention have been set forth for the purpose of disclosure, modifications of the disclosed embodiments of the invention as well as other embodiments thereof may occur to those skilled in the art. The scope of the claims should not be limited by the preferred embodiments set forth in the examples, but should be given the broadest interpretation consistent with the description as a whole.

What is claimed is:

1. A fragrance delivery apparatus comprising: a body, a fan, a power base, and a case;
   the body including an accommodation chamber defined in the body, a receiving groove formed above the accommodation chamber, an air vent arranged on a first side of the body and communicating between the accommodation chamber and the receiving groove, and multiple elongated orifices formed on a second side of the body opposite to the first side of the body and communicating with the accommodation chamber of the body;

the fan being accommodated in the accommodation chamber and drawing external gas from the multiple elongated orifices;

the power base being connected with a bottom of the body and shielding the accommodation chamber, and the power base being configured to supply power and being electrically connected with the fan; and the case being removably connected outside the body and including a spray nozzle defined on a side of the case, wherein the spray nozzle is in communication with the receiving groove, wherein a solid fragrance member is housed in the fragrance delivery apparatus and is configured to absorb aromatic substance.

2. The fragrance delivery apparatus as claimed in claim 1, wherein the solid fragrance member has a bored carrier and multiple through orifices, and the bored carrier is configured to absorb the aromatic substance, wherein the multiple through orifices pass through two ends of the bored carrier.

3. The fragrance delivery apparatus as claimed in claim 1, wherein the body further includes a stepped portion formed on an outer wall thereof, and the case is hollow and covers on the outer wall of the body, wherein an inner wall of the case is detachably connected on the body, and the stepped portion matingly couples inside a bottom of the case.

4. The fragrance delivery apparatus as claimed in claim 1, wherein the fragrance delivery apparatus further comprises a stop member including an opening defined in the stop member and mating with the fan, wherein the stop member is connected on the fan and the opening corresponds to the fan, such that a peripheral portion of the stop member around the opening couples with the inner wall of the body so as to shield a gap between the opening and the accommodation chamber.

5. The fragrance delivery apparatus as claimed in claim 4, wherein the stop member includes multiple affix extensions extending outwardly from a bottom of thereof so as to retain with the fan.

6. The fragrance delivery apparatus as claimed in claim 1, wherein the fragrance delivery apparatus further comprises a circuit board, a light emitting element, a light guide sheet, and a power switch; wherein the circuit board is electrically connected with the fan, the power base, the light emitting element, and the power switch; the circuit board is mounted on the power base in the body, and the light guide sheet is fixed on the circuit board and covers the light emitting element, wherein each of the body and the case is made of transparent material or translucent material.

7. A fragrance delivery apparatus comprising: a body, a fan, a power base, and a case;

the body including an accommodation chamber defined in the body, a receiving groove formed above the accommodation chamber, an air vent arranged on a first side of the body and communicating between the accommodation chamber and the receiving groove, and multiple elongated orifices formed on a second side of the body opposite to the first side of the body and communicating with the accommodation chamber of the body;

the fan being accommodated in the accommodation chamber and drawing external gas from the multiple elongated orifices;

the power base being connected with a bottom of the body and shielding the accommodation chamber, and the power base being configured to supply power and being electrically connected with the fan; and the case being removably connected outside the body and including a spray nozzle defined on a side of the case, wherein the spray nozzle is in communication with the receiving groove, wherein the fragrance delivery apparatus further comprises a support loop including multiple abutting ribs arranged around an outer wall of the support loop, the case is hollow, and the support loop is fitted on the outer wall of the body and the case covers on the outer wall of the body, wherein an inner wall of the body is detachably connected with the multiple abutting ribs of the support loop, such that when the case covers on the outer wall of the body, the inner wall of the body forces the multiple abutting ribs to deform and to engage with the inner wall of the case, and the case removably engages with the support loop, thus removing/covering the case from/on the body.

8. The fragrance delivery apparatus as claimed in claim 7, wherein a solid fragrance member is housed in the fragrance delivery apparatus and is configured to absorb aromatic substance.

9. The fragrance delivery apparatus as claimed in claim 8, wherein the solid fragrance member has a bored carrier and multiple through orifices, and the bored carrier is configured to absorb the aromatic substance, wherein the multiple through orifices pass through two ends of the bored carrier.

10. The fragrance delivery apparatus as claimed in claim 7, wherein the body further includes a stepped portion formed on an outer wall thereof, and the case is hollow and covers on the outer wall of the body, wherein an inner wall of the case is detachably connected on the body, and the stepped portion matingly couples inside a bottom of the case.

11. The fragrance delivery apparatus as claimed in claim 7, wherein the fragrance delivery apparatus further comprises a stop member including an opening defined in the stop member and mating with the fan, wherein the stop member is connected on the fan and the opening corresponds to the fan, such that a peripheral portion of the stop member around the opening couples with the inner wall of the body so as to shield a gap between the opening and the accommodation chamber.

12. The fragrance delivery apparatus as claimed in claim 11, wherein the stop member includes multiple affix extensions extending outwardly from a bottom of thereof so as to retain with the fan.

13. The fragrance delivery apparatus as claimed in claim 7, wherein the fragrance delivery apparatus further comprises a circuit board, a light emitting element, a light guide sheet, and a power switch; wherein the circuit board is electrically connected with the fan, the power base, the light emitting element, and the power switch; the circuit board is mounted on the power base in the body, and the light guide sheet is fixed on the circuit board and covers the light emitting element, wherein each of the body and the case is made of transparent material or translucent material.

14. A fragrance delivery apparatus comprising: a body, a fan, a power base, and a case;

the body including an accommodation chamber defined in the body, a receiving groove formed above the accommodation chamber, an air vent arranged on a first side of the body and communicating between the accommodation chamber and the receiving groove, and multiple elongated orifices formed on a second side of the body opposite to the first side of the body and communicating with the accommodation chamber of the body;

the fan being accommodated in the accommodation chamber and drawing external pas from the multiple elongated orifices;

the power base being connected with a bottom of the body and shielding the accommodation chamber, and the power base being configured to supply power and being electrically connected with the fan; and the case being removably connected outside the body and including a spray nozzle defined on a side of the case, wherein the spray nozzle is in communication with the receiving groove, wherein the receiving groove of the body has multiple flaps separately arranged on a bottom thereof, and the receiving groove has a recessed guiding portion formed on the bottom thereof below the multiple flaps.

15. The fragrance delivery apparatus as claimed in claim 14, wherein a solid fragrance member is housed in the fragrance delivery apparatus and is configured to absorb aromatic substance.

16. The fragrance delivery apparatus as claimed in claim 15, wherein the solid fragrance member has a bored carrier and multiple through orifices, and the bored carrier is configured to absorb the aromatic substance, wherein the multiple through orifices pass through two ends of the bored carrier.

17. The fragrance delivery apparatus as claimed in claim 14, wherein the body further includes a stepped portion formed on an outer wall thereof, and the case is hollow and covers on the outer wall of the body, wherein an inner wall of the case is detachably connected on the body, and the stepped portion matingly couples inside a bottom of the case.

18. The fragrance delivery apparatus as claimed in claim 17, wherein the stop member includes multiple affix extensions extending outwardly from a bottom of thereof so as to retain with the fan.

19. The fragrance delivery apparatus as claimed in claim 14, wherein the fragrance delivery apparatus further comprises a stop member including an opening defined in the stop member and mating with the fan, wherein the stop member is connected on the fan and the opening corresponds to the fan, such that a peripheral portion of the stop member around the opening couples with the inner wall of the body so as to shield a gap between the opening and the accommodation chamber.

20. The fragrance delivery apparatus as claimed in claim 14, wherein the fragrance delivery apparatus further comprises a circuit board, a light emitting element, a light guide sheet, and a power switch; wherein the circuit board is electrically connected with the fan, the power base, the light emitting element, and the power switch; the circuit board is mounted on the power base in the body, and the light guide sheet is fixed on the circuit board and covers the light emitting element, wherein each of the body and the case is made of transparent material or translucent material.

* * * * *